United States Patent [19]

Möhrke et al.

[11] 3,930,500

[45] Jan. 6, 1976

[54] PHARMACEUTICAL SINGLE-DOSE CONTAINER FOR THE EYE

[75] Inventors: Klaus Möhrke; Heinrich Eggert; Helmut Franz, all of Biberach an der Riss; Dieter Jarsen, Laupheim, all of Germany

[73] Assignee: Boehringer Ingelheim GmbH, Ingelheim am Rhein, Germany

[22] Filed: Mar. 28, 1973

[21] Appl. No.: 345,745

[30] Foreign Application Priority Data

| | | |
|---|---|---|
| Mar. 29, 1972 | Germany | 2215215 |
| Dec. 18, 1972 | Germany | 2261913 |
| Sept. 13, 1972 | Germany | 7233642[U] |
| Dec. 18, 1972 | Germany | 7246257[U] |

[52] U.S. Cl. .................. 128/233; 128/249; 222/106

[51] Int. Cl.$^{2}$ .......................................... A61M 7/00

[58] Field of Search ........... 222/541, 543, 563, 107, 222/510, 89, 92, 209, 501, 518, 568, 540, 560, 561, 526, 544; 220/38.5, 49; 128/249, 272, 216, 233, 232; 206/498; 229/66, 86, 51 D

[56] References Cited

UNITED STATES PATENTS

| | | | |
|---|---|---|---|
| 1,438,487 | 12/1922 | Greene | 222/541 UX |
| 2,044,327 | 6/1936 | Quimby | 220/49 |
| 2,293,952 | 8/1942 | Stroop | 229/51 S |
| 2,397,051 | 3/1946 | Scherer | 222/107 X |
| 2,648,463 | 8/1953 | Scherer | 222/541 X |
| 2,847,010 | 8/1958 | Knight | 128/249 |
| 3,094,269 | 6/1963 | Schneider | 229/51 S X |
| 3,255,925 | 6/1966 | Park | 222/563 X |
| 3,797,493 | 3/1974 | Saudek | 229/86 X |

FOREIGN PATENTS OR APPLICATIONS

| | | | |
|---|---|---|---|
| 971,137 | 9/1964 | United Kingdom | 128/233 |
| 1,018,526 | 10/1952 | France | 222/92 |
| 1,204,753 | 9/1970 | United Kingdom | 222/92 |
| 285,893 | 2/1965 | Netherlands | 222/386.5 |

*Primary Examiner*—Robert B. Reeves
*Assistant Examiner*—Charles A. Marmor
*Attorney, Agent, or Firm*—Hammond & Littell

[57] ABSTRACT

A pharmaceutical single-dose container consisting essentially of an elongate flexible closure member extending through the wall of the container and sealed therein with part of said closure member extending outwardly of the container, said part being engageable by hand to permit the closure member to be pulled out of the container wall thereby to provide a discharge opening through which the contents of the container can be discharged.

3 Claims, 19 Drawing Figures

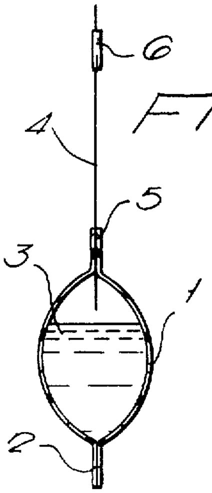
FIG.1.
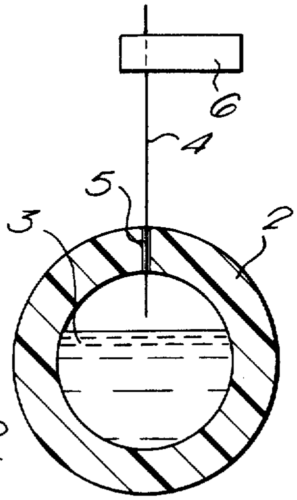
FIG.2.
FIG.3.
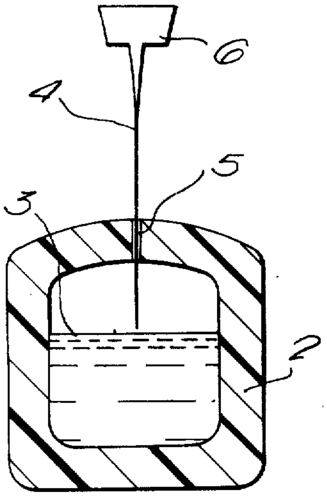
FIG.4.
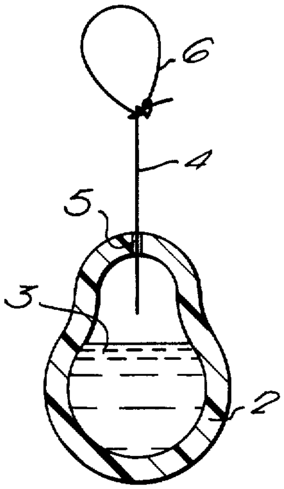

PHARMACEUTICAL SINGLE-DOSE CONTAINER FOR THE EYE

This invention relates to expendible sealed containers whose contents, such as solutions, ointments, emulsions, syrups, powders and other like products capable of fluid flow, may be discharged preferably as a single dose when the container is opened. Such containers will hereinafter be referred to as "containers of the kind described."

THE PRIOR ART

Some known containers of the kind described have a discharge channel, through which the contents may be discharged, the channel being covered by a nipple of, for example, ball or vaned shaped. The nipple can be torn from the container to expose the discharge channel by twisting it relative to the rest of the container. There is a risk, however, of projecting burrs remaining around the discharge channel when the nipple is removed; this may be dangerous where, for example, the contents are to be discharged into an eye. There is also a risk that material broken off when the nipple is removed may block the channel.

Other known containers of the kind described, formed by joining together container walls along their edges by means of welded or adherent seams, may be opened by cutting through the seam with a suitable instrument, such as scissors or a knife. The instrument used for cutting may, however, contaminate the contents of the container. Further, a cutting instrument may not always be readily available when it is desired to open a container.

THE INVENTION

The present invention provides a container of the kind described having an elongate flexible closure member extending through the wall of the container and sealed therein with part of said closure member extending outwardly of the container, said part being engageable by hand to permit the closure member to be pulled out of the container wall, thereby to provide a discharge opening through which the contents of the container can be discharged.

Since said closure member can be removed by hand, it is not necessary to use a cutting instrument to provide a discharge opening; and since it is not necessary to tear off a nipple or any part of the container wall to provide a discharge opening, there is less danger of projecting burrs being left around the discharge opening or of the discharge opening being blocked.

Said closure member can be sealed in the discharge opening in any suitable manner, for example, by welding it to the container walls, by heat-sealing or by adhesive. As suitable elongate closure members we may mention, for example, a thread, string, fiber, strip, tape, wire, rod or the like. The closure member is preferably formed as a thread of plastic material or of metal foil, although cellulose glass or glass threads, or threads of cotton or silk which have been impregnated or coated with a plastic compound, may be employed.

In a preferred embodiment, the container of the present invention comprises two plastic or plastic-coated metal foils forming the container wall and sealed together at their edges by a welded, heat-sealed or adherent seam. In the formation of such a container a closure member is positioned between the foils prior to the seaming operation so that when seaming takes place, the seam serves to secure and seal the closure member in the container wall. When it is desired to open the container, the member may be pulled and removed from the seam, thereby providing an opening in the seam through which the contents of the container can be discharged. The foils may then be squeezed together so as to force the contents through the discharge opening.

If the container is relatively small, the foils are preferably deep-drawn before the contents are introduced to the container.

Containers with a rigid wall may, if desired, be employed, a prefabricated discharge opening being provided which is sealed, for example, with a suitably shaped aluminum wire.

In order to facilitate the pulling of said closure member from the container wall, the outer part of said member may be provided with gripping means, for example by looping it or connecting a suitable gripping member, so that the closure member may be the more easily gripped. The surface of the gripping member may be ridged, for example by embossing, as may surface or flats provided on the container wall to facilitate the holding of the container wall during the opening procedure. Such surfaces or flats may be provided at the edge of the container walls so as to ensure that the contents of the container are not discharged prematurely by squeezing the container walls while said closure member is being removed.

Preferably, the part of the closure member extending outwardly of the container is welded, heat-sealed or otherwise embedded in a portion of the container wall covering the discharge opening. In addition to preventing the closure member from being accidentally pulled, this portion also serves as a hand grip to facilitate opening of the container. If the grip portion is torn from the container by a rotary or shearing movement, then said closure member is simultaneously removed so as to provide a discharge opening. The grip portion can be torn from the container more easily if at the point of connection between it and the rest of the container a predetermined fracture region, provided for example by a line of indentations or perforation, is provided.

As a sharp-edged or burred fracture can easily result when the grip portion is torn from the rest of the container which during application for example to the eye can cause injury, it is preferable to provide an adaptor member in the form of a collar of a soft material, such as wax or a soft plastic, surrounding the fracture region. The adaptor member surrounds the fracture region in such a way as to project outwardly from the discharge opening, thereby to ensure that sharp-edged or burred fracture points cannot contact sensitive parts of a body during application of the contents. The adaptor member is preferably sealed to the container walls to ensure that the contents cannot leak from between the container walls and the adaptor member during discharge of the contents.

In a further preferred embodiment, wherein no grip portion is provided, an adaptor member formed as a cap covering and surrounding the discharge opening has a central discharge channel communicating with the discharge opening and in which the part of the closure member extending from the container wall is disposed and projects therefrom. The adaptor member is preferably of conical shape, tapering from its base around the discharge opening to its tip remote from the container wall. In use, the closure member may be pulled from the discharge channel and opening. If the discharge channel is sufficiently narrow, the contents may be emitted from the container as a spray. The adaptor member is preferably made of plastic, so that the adaptor can advantageously be heated and sealed on to the container in the desired position after the sealing of the container. Wax may also be suitable for simple designs of the adaptor member. To ensure that the adaptor member is securely located, ribs, lugs or teeth may be provided on the container wall beneath the discharge opening, which project into the adaptor member and thus rigidly anchor the adaptor member to the container wall.

Preferred embodiments of the invention will hereinafter be described merely by way of example with reference to the accompanying drawings in which:

FIG. 1 is a sectional view of a first embodiment of a container of the present invention;

FIG. 2 is a further sectional view of the first embodiment at right angles to the sectional view of FIG. 1;

FIG. 3 is a sectional view of a second embodiment having a gripping member connected to the part of the closure member extending from the container wall;

FIG. 4 is a sectional view of a third embodiment having a loop formed in the projecting part of the closure member;

Figure 10A:
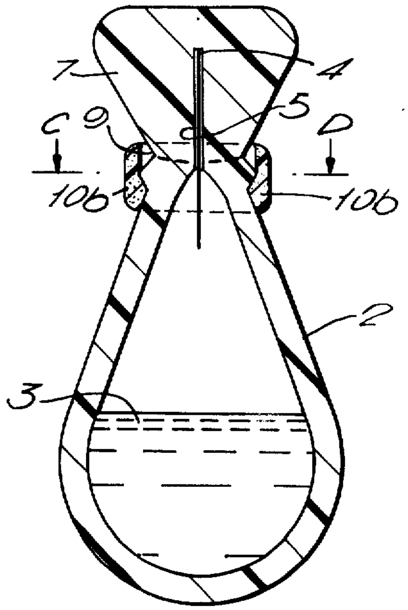
FIG. 10A is a sectional view of a ninth embodiment having a hand grip portion which covers and an adaptor member which surrounds the discharge opening.
Figure 10C:
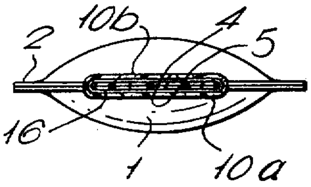
FIG. 10C is a sectional view along line C–D of FIG. 10A.
Figure 10B:
FIG. 10B is a sectional view of the ninth embodiment at right angles to the view of FIG. 10A.
Figure 12A:
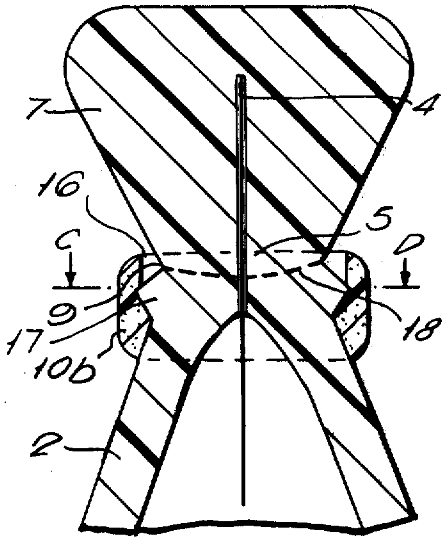
Figure 13A:
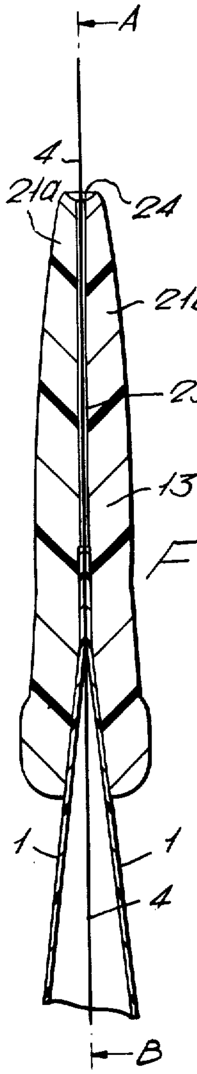
Figure 13B:
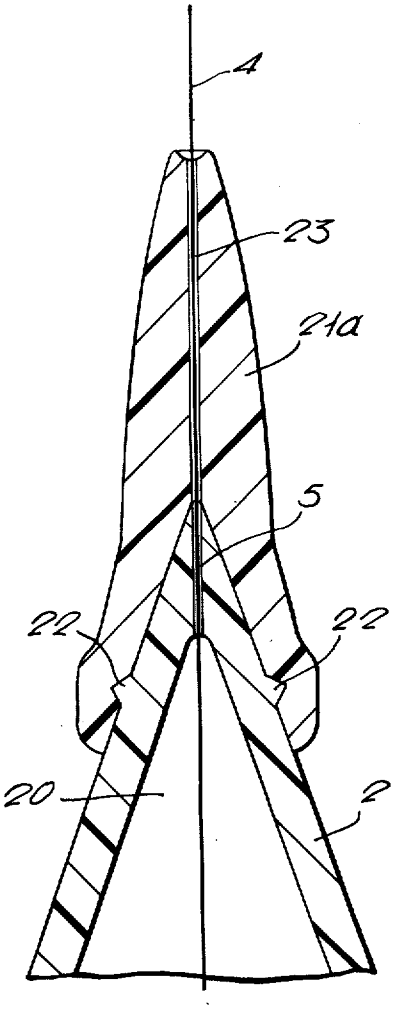

FIGS. 12A, B and C are enlargements of the parts of the ninth embodiment adjacent the discharge opening, and correspond to the views of FIGS. 10A, B and C, respectively;

FIG. 13A is a sectional view of part of a tenth embodiment adjacent the discharge opening, this embodiment having no hand grip portion, but having a conically shaped adaptor member in the form of a cap; and FIG. 13B is a sectional view along line A-B of FIG. 13A.

Referring to FIGS. 1 and 2, the first embodiment shown consists of a container formed from two foils 1 forming the container walls made of plastic or plastic-coated metal, joined together at their edges by a welded, or adhesive seam 2. In the formation of the container, the contents 3 of the container (e.g. liquid or other substance capable of fluid flow) are introduced, and an elongate flexible closure member comprising a thread 4, preferably made of plastic or metal foil, is positioned between the foils 1 so that part of the thread 4 projects into and part projects outwardly from the foils. When the seam is formed, thread 4 is also secured and sealed in the seam as at 5. A flat grip member 6 is secured to thread 4.

When it is desired to discharge the contents 3, the grip member 6 is gripped between the fingers of one hand and part of seam 2 is gripped between the fingers of the other. Thread 4 is then pulled and removed from seam 2. The aperture thus formed at 5 in seam 2 serves as a discharge opening, and by squeezing the container walls together, contents 3 may be discharged as a single dose.

In subsequent embodiments, parts corresponding to parts of the first embodiment will be denoted by the same reference numeral.

The second and third embodiments shown in FIGS. 3 and 4 are generally similar to the first embodiment, although the shapes of the container are different. The major difference, however, of the second embodiment shown in FIG. 3 relative to the first embodiment is that thread 4 is provided at its outer end with an integral enlarged portion 6 which serves as a grip member; and in the third embodiment of FIG. 4 the outer end of the thread 4 is looped at 6 to facilitate gripping of the thread.

Figure 5:
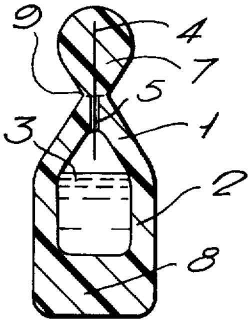
FIG. 5 is a sectional view of a fourth embodiment having its discharge opening covered by a hand grip portion.

Referring to the fourth embodiment shown in FIG. 5, the container is formed in a generally similar manner to the first embodiment shown in FIGS. 1 and 2. Foils 1 are, however, provided with integral projecting lobes 7 which are joined together face-to-face during the seaming operation to serve as a hand grip portion enclosing the outer end of a thread 4 and covering a discharge opening at 5. The lower end of seam 2 remote from opening 5 is widened as at 8 to facilitate gripping when the container is opened.

When the container is opened, the hand grip portion is gripped between the fingers and is torn from the rest of the container at a neck portion 9; the neck portion 9 may be indented or perforated to facilitate tearing. As the grip portion is torn from the container, thread 4 is removed from the container wall. A discharge opening is thus provided at 5 and the contents 3 may be discharged.

Figure 6:
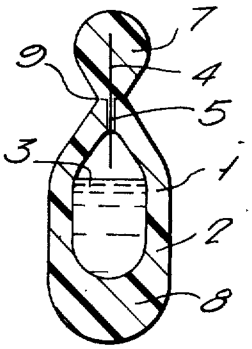
FIG. 6 is a sectional view of a fifth embodiment, generally similar to the embodiment of FIG. 5.

The fifth embodiment shown in FIG. 6 is generally similar to the fourth embodiment; the widened portion at 8 of seam 2 is, however, shaped differently, being rounded.

Figure 7:
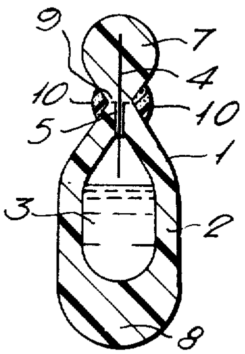
FIG. 7 is a sectional view of a sixth embodiment having an adaptor member surrounding the hand grip portion.

The sixth embodiment shown in FIG. 7 is similar to the fifth embodiment, but incorporates a wax collar or adaptor member 10 surrounding the neck 9 at which grip portion 7 is torn. The collar 10 projects outwardly from neck 9 so as to ensure that sharp edges or burrs, arising when the grip portion 7 is torn, are not exposed.

Figure 8:
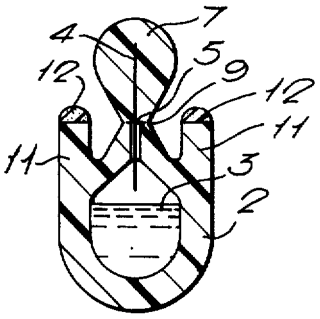
FIG. 8 is a sectional view of a seventh embodiment adapted for use in applying medicaments to the eye.

The seventh embodiment shown in FIG. 8 is designed specifically for treating the eye, and the contents 3 may be, for example, an eye lotion. The embodiment is similar to those shown in FIGS. 5 and 6 in that it incorporates a hand grip portion. It differs however in that the foils 1 are each provided with projecting parts 11 on either side of thread 4, the parts of the foils on the same side of thread 4 being joined together face-to-face when the foils 1 are seamed together. The extremities of parts 11 are so spaced that each extremity may be located in the corner of an eye when the contents 3 are discharged into the eye. The extremities are provided with a protective plastic or wax layer 12 to prevent damage to the eye. The bases of the projecting parts 11 also serve as finger grips when the container is opened.

Figure 9:
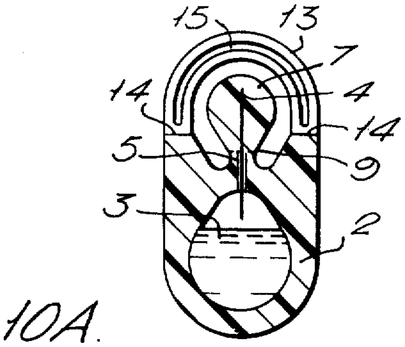
FIG. 9 is a sectional view of an eighth embodiment, also adapted for use in applying medicaments to the eye.

In the eighth embodiment shown in FIG. 9 the foils 1 are provided with loop portions 13 extending from one side of the thread 4 to the other side of thread 4. Although positioned face-to-face, these looped portions 13 are not joined together during the seaming operation so that they can subsequently be bent away from each other. The loop portions 13 are dimensioned so that when they are bent away from each other about their points of connection at 14 to seam 2, they can serve as a supporting frame surrounding an eye to provide support and location for the container when the contents are discharged into an eye. Each loop portion 13 is preferably embossed to provide a central ridge as at 15 to provide a certain amount of rigidity to the loop portions.

Referring now to the ninth embodiments shown in FIGS. 10A to 12C, the embodiment is generally similar to the sixth embodiment shown in FIG. 7, and in particular has a hand grip portion 7 whose neck 9 is surrounded by an adaptor member in the form of a wax or plastic collar 10. The collar is formed as a split member comprising two identical halves 10*a* and 10*b*.

Figure 12B:
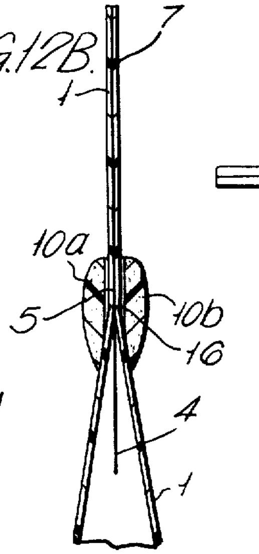
Figure 12C:
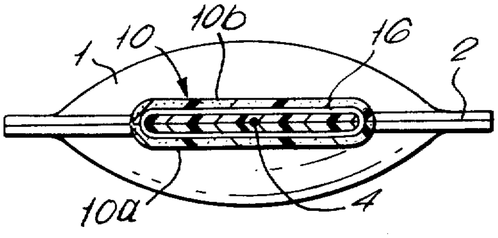

The shape of parts 10*a* and 10*b* is best shown in FIG. 12B. It can be seen that the upper portions of the inner surface of parts 10*a* and 10*b* define an annular opening 16, as shown in FIG. 12C, which serves to increase the accuracy of application of the contents of the container. The lower portions of parts 10*a* and 10*b* are tapered to accomodate the shape of the container. The parts 10*a* and 10*b* are welded together in situ after the seaming of foils 1, and the tapered lower portions of 10*a* and 10*b* are sealed, by welding, pressing or adhesion, to foils 1 to prevent the contents from seeping between the adaptor member and the container wall when the contents are discharged. Projecting teeth 17 integral with the foil edges are located in the inner wall of collar 10 during the interconnection of parts 10*a* and 10*b*, and teeth 17 serve to secure the adaptor member 10 to the container wall.

Figure 11A:
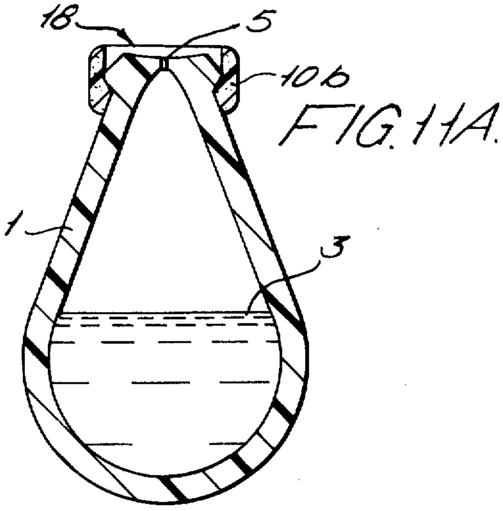
FIG. 11A is a sectional view of the ninth embodiment corresponding to FIG. 10A, showing the container open.
Figure 11B:
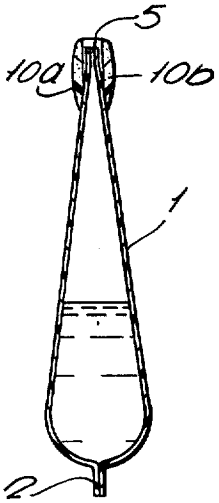
FIG. 11B is a sectional view of the ninth embodiment at right angles to the view of FIG. 11A.

The adaptor member projects from the container wall above neck 9 of the hand grip portion 7, neck 9 being perforated as at 18 to define a predetermined fracture region in which the hand portion can be torn from the rest of the container. Hence, resultant burrs and sharp edges will not be exposed when the hand grip portion 7 and closure member 4 are removed, as shown in FIGS. 11A and 11B. When the hand grip portion 7 is torn, the collar 10 can serve as a means for gripping the container.

The tenth embodiment shown in FIGS. 13A and 13B is formed in a similar manner to that of the first embodiment. Foils 1 are, however, shaped to provide a tapered portion 20, the thread 4 being secured and sealed in the seam 2 at the apex of the tapered portion. A wax or plastic adaptor member 21 of generally conical shape is located on the tapered portion 20 by means of retaining teeth 22 projecting from the edges of foils 1 and engaging the inner surface of member 21. Member 21 is formed as a split member comprising two identical halves 21*a* and 21*b* which are welded, heat-sealed or adhesively joined together in situ in the manner of the adaptor member of the first embodiment. The inner surface of the base of member 21 is sealed to the container wall and is tapered to accommodate the shape of the container wall.

The adaptor member 21 is formed to provide a discharge channel 23 communicating with the discharge opening at 5 and in which thread 4 is disposed. The end of thread 4 extends from outlet 24 of channel 23 which is widerend, as shown. When thread 4 is pulled from the discharge channel, the contents of the container may be discharged through the channel. As a result of the narrowness of the channel, the contents may be emitted as a spray if they are of suitable liquidity. The shape of adaptor member 21 facilitates the accurate application of the spray.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A pharmaceutical single-dose container adapted for applying the contents thereof to an eye, said container having been formed by placing two foils face-to-face, positioning an elongate flexible closure member there between, and joining and sealing together the edges of said foils by a seam to form a container wall, said seam serving to secure and seal said closure member in the container wall, said closure member extending through the wall of the container and sealed therein with part of said closure member extending outwardly of the container, said part being engageable by hand to permit the closure member to be pulled out of the container wall to provide a discharge opening through which the contents of the container can be discharged, said seam being widened to seal said outwardly extending part of said closure member therein, said foils being each provided with looped portions extending from one side of said closure member to the opposite side, the looped portions being bendable to positions in which they define a supporting frame for positioning around an eye.

2. A container of claim 1 adapted for applying said contents to an eye, wherein said looped portions are dimensioned so that they are bent away from each other about their points of connection at said seam.

3. A container of claim 1 adapted for applying said contents to an eye, wherein each looped portion is embossed to provide a central ridge for providing rigidity to said looped portions.

* * * * *